United States Patent [19]

Mezey et al.

[11] 4,322,394

[45] Mar. 30, 1982

[54] ADSORBENT REGENERATION AND GAS SEPARATION UTILIZING MICROWAVE HEATING

[75] Inventors: Eugene J. Mezey; Salvatore T. Dinovo, both of Columbus, Ohio

[73] Assignee: Battelle Memorial Institute, Columbus, Ohio

[21] Appl. No.: 178,251

[22] Filed: Aug. 12, 1980

Related U.S. Application Data

[63] Continuation-in-part of Ser. No. 846,798, Oct. 31, 1977, abandoned.

[51] Int. Cl.$^3$ .............................................. C01B 17/00
[52] U.S. Cl. ................................... 423/244; 423/230; 423/659; 423/563; 423/437; 252/411 R; 55/33; 55/208
[58] Field of Search .......... 423/242 A, 242 R, 244 A, 423/244 R, 230, 437, 539, 563; 252/411 R, 411 S; 55/25, 26, 27, 28, 33, 208; 585/826

[56] References Cited

U.S. PATENT DOCUMENTS

| | | | |
|---|---|---|---|
| 984,498 | 2/1911 | Sprague | 423/244 |
| 3,359,707 | 12/1967 | Jean | 55/33 |
| 3,771,234 | 11/1973 | Forster | 34/1 |
| 4,011,306 | 3/1977 | Fox | 423/579 |
| 4,038,050 | 7/1977 | Lowther | 55/18 |

FOREIGN PATENT DOCUMENTS

| | | |
|---|---|---|
| 2107717 | 8/1972 | Fed. Rep. of Germany ........ 55/208 |
| 51-43394 | 4/1976 | Japan .. |
| 51-43395 | 4/1976 | Japan . |
| 51-145491 | 12/1976 | Japan . |
| 1543160 | 3/1979 | United Kingdom . |

*Primary Examiner*—Earl C. Thomas
*Assistant Examiner*—Gregory A. Heller
*Attorney, Agent, or Firm*—Kenneth R. Warburton

[57] ABSTRACT

Dielectric heating with microwaves of saturated solid noncarbon adsorbents to remove the adsorbed materials results in more rapid, efficient and safe regeneration than conventional heating. The microwaves heat the adsorbents internally and in the absence of spark discharges without thermal and mechanical degradation of the adsorbent, and also in the absence of activating gas bring the adsorbents to a temperature sufficient to desorb the adsorbate. Separation of a gas mixture into two concentrated streams of its components is enabled by adsorption of one fraction by a selective adsorbent followed by removal of that fraction with dielectric heating and little or no purge gas. Useful by-products of the separation process are thereby economically recovered.

10 Claims, 1 Drawing Figure

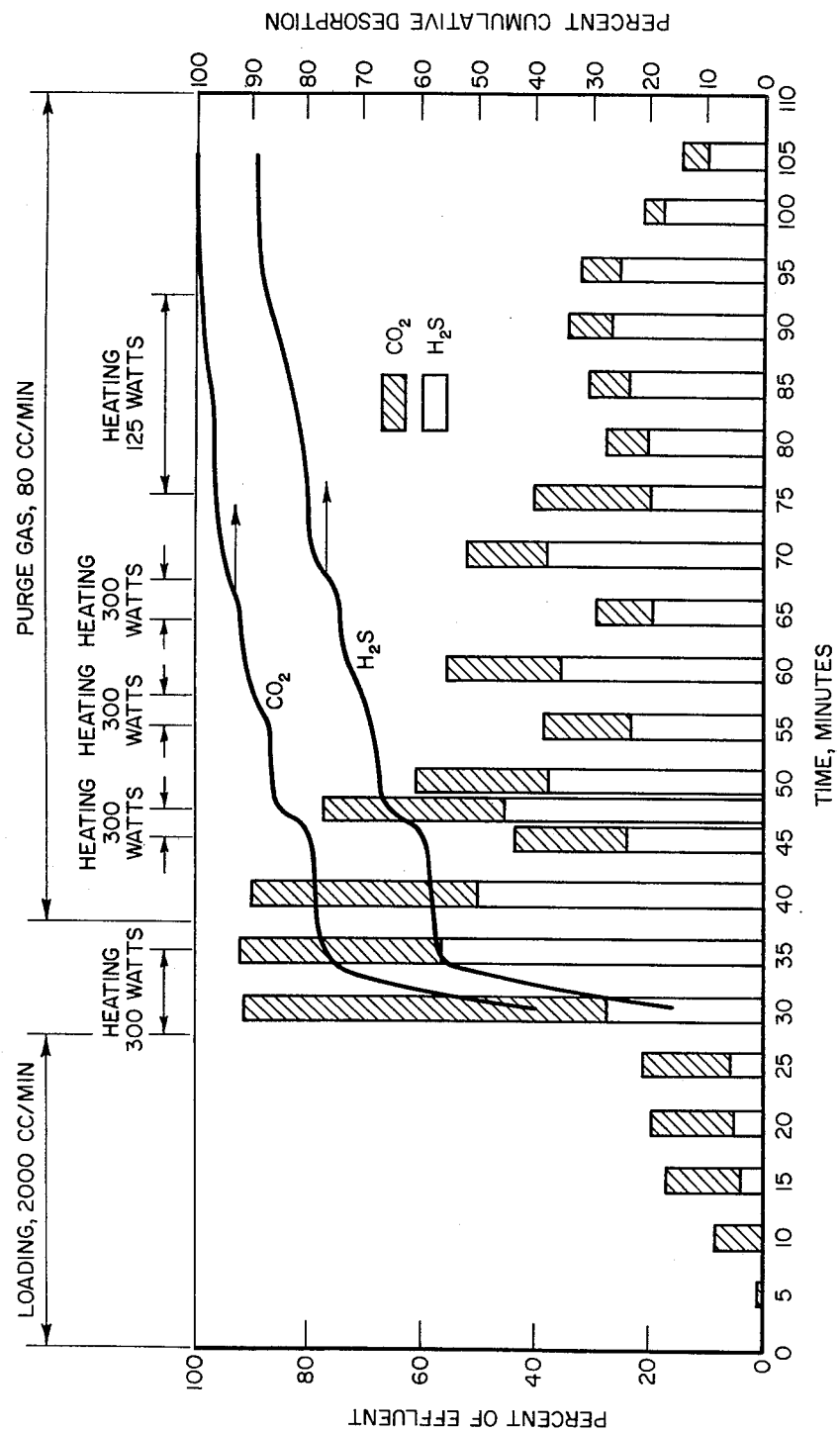

ADSORBENT REGENERATION AND GAS SEPARATION UTILIZING MICROWAVE HEATING

CROSS REFERENCE TO RELATED APPLICATION

This is a continuation-in-part of our U.S. patent application Ser. No. 846,798, filed Oct. 31, 1977, and now abandoned.

TECHNICAL FIELD

Adsorbents are solid materials used to selectively remove contaminants or components from fluid process streams. Activated charcoal, zinc oxide, activated alumina, and molecular sieves are typical examples of the variety of known adsorbents. The adsorbent may be self-supporting or may be fixed to a substrate. The process stream is caused to contact the adsorbent for the required time period for the desired removal of the contaminant or component. The adsorbent may also be used to effect a separation of a gas stream into two components if, after removal of one component, the flow of the process stream is stopped long enough to desorb and recover the adsorbed component.

Even if the adsorbed material is not recovered for further use (e.g., it may merely be a contaminant and not a useful by-product of the separation process), it still must be removed periodically after it saturates the adsorbent or the adsorbent will cease its function. One method of regeneration is by heating the adsorbent (and substrate) to a temperature sufficient to desorb the adsorbate. Typically, this heating is accomplished with a flow of hot gas since it not only heats the adsorbent, but also purges the adsorbate as it is desorbed.

Effective adsorbents create a problem in regeneration since, generally, the more effective the adsorbent, the more difficult it is to remove the adsorbate. Long regeneration times and large purge gas volumes are therefore required for a moderate temperature purge gas to desorb the adsorbate. This is due in part to the poor thermal transport inherent in this method and with these adsorbent and substrate materials. Moreover, heat requirements are high since not only the adsorbent (which can be very large in itself) but also the adsorbent support, the adsorbent column associated conduits and large quantities of purge gas often must be heated. The long regeneration times are poor on efficiency and large volumes of purge gas result in effluents which are very dilute in the adsorbed (desorbed) component. Usefulness of the adsorbed component as a by-product is thereby reduced since more processing would be required to recover the component from the dilute gas.

Higher temperature purge gas could be used for more rapid desorption but this may also degrade the adsorbent capacity and shorten the life of the support. Large volumes of purge gas and dilute off-gas would still result.

BACKGROUND ART

The present invention provides dielectric heating which eliminates the problems and provides benefits unobtainable with hot purge gas heating and with conventional heating, and with an energy savings.

In the prior art, dielectric heating (in particular, microwave heating) has been suggested for many heating processes including drying, vulcanization of rubber, detoxification of dangerous substances and polymerization of fiberglass laminates. For example, U.S. Pat. No. 3,771,234 suggests the use of microwave radiation for removing volatile polar vehicles from non-polar materials (dielectric loss factors of about 0.0001 to 0.1), specifically drying of synthetic polymers.

Conventional heating plus a purge gas flow is also used (see U.S. Pat. No. 4,011,306), but as a result of poor heat transfer this can require long regeneration times or high temperatures. German Offenlegungschrift No. 2,107,717 describes a particular circulation system for moving an activated charcoal through an adsorption reactor and then through a regeneration reactor, wherein microwave energy is applied for releasing adsorbed gases, and then the charcoal is recirculated back again through the adsorption reactor. It is inherent from such continued circulation of the charcoal adsorbent that the charcoal is readily subject to attrition and mechanical degradation. Microwave heating in the presence of an added regenerating or purge gas, such as steam, for regenerating carbon adsorbents apparently is disclosed in Japanese Kokai Nos. 76/43,394 and 76/43,395. These Kokai also reveal that only certain active carbons are receptive to microwave heating of an extent adequate for desorption and regeneration with the heat treatment history of the carbon adsorbent affecting and determining whether desorption by microwaves be operable. Japanese Kokai No. 76/145,491 concerns regenerating an activated carbon through exposure to a high frequency electrical field to remove adsorbed substances by small discharge plasma.

The prior art also includes, such as described in U.S. Pat. No. 4,038,050, an electrical desorption of molecular sieve adsorbents wherein during desorption-regeneration there is provided an electrical current flow from one electrode and then from particle to particle of the adsorbent to another electrode.

As is well known in the art, heating with microwaves provides high frequency oscillatory movement of the molecules within the material by the combined interaction of the electric and magnetic fields associated with absorbed electromagnetic energy. The rapid temperature increase of the material is caused by this molecular friction.

DISCLOSURE OF THE INVENTION

It is an object of the invention to provide a process for the rapid thermal regeneration of adsorbents so that throughput of process streams can be increased or the amount of adsorbent can be reduced.

It is also an object to provide rapid regeneration of adsorbents with little to no degradation of adsorbent or support.

It is further an object of the invention to provide a process of separating a fluid process stream into two concentrated component streams whereby both streams can be economically treated and used.

It is an object of the invention to provide the above benefits while using less energy than with conventional forms of heating.

In accordance with the objectives, the invention is a process for the rapid, thermal regeneration of adsorbents wherein the saturated adsorbent is heated dielectrically to desorb the adsorbate, after which a small quantity of purge gas stream may flush the adsorbate from the area of the adsorbent. Heating dielectrically, with microwave radiation, effects internal heating of the adsorbent thereby minimizing the effects of poor heat transfer of the absorbent and substrate which delays the effectiveness of a conventional form of heating. Consequently, this is not a mere substitution of one heat source for another, but the provision for a different form of heating which may lower energy usage and, at the same time, benefit the process in allowing selective, rapid heating of the absorbent, rapid desorption of adsorbed components and gas separation into two concentrated streams.

Advantageously the invention is practiced, i.e. microwave heating applied, while the saturated adsorbent is within its absorber reactor chamber and without removal therefrom. In this manner the invention avoids significant attrition and mechanical degradation of the adsorbent arising from transporting or moving adsorbent to a separate chamber or apparatus for adsorbate removal and adsorbent regeneration. Mechanical degradation generally is evidenced by an altered physical form of the adsorbent, such as pellets or granules fragmenting, chipping or the like.

The inherent nature of microwave heating of heating the adsorbent internally avoids significant thermal degradation. Thermal degradation is evidenced by a failure of the adsorbent to retain the substantial equivalent of its original adsorption properties.

Further, the invention can be used to desorb materials which are physically adsorbed on the adsorbent and also to desorb chemisorbed materials which may have further undergone chemical reaction with the adsorbent. An example of the latter "absorption" is the reaction of $SO_2$ in flue gases with a modified ZnO absorbent.

The effects of dielectric heating are also utilized in separating a fluid mixture into two or more concentrated component streams. Each repetition of the inventive process may result in separation into two components. Successive treatments over different adsorbents may eventually reduce a fluid mixture to many of its individual components.

In the separation method, the fluid mixture is passed over an adsorbent which preferentially adsorbs at least one component thereof. The component is adsorbed as the mixture passes and the fluid stream remaining after adsorption is collected. This effluent stream is more concentrated than the input fluid mixture in components other than those removed by the adsorption. Thereafter, or after the adsorbent is saturated with the adsorbate, the fluid mixture flow over the absorber is temporarily halted and the absorbent is heated dielectrically to a temperature at which the adsorbed component desorbs (or to a temperature at which the "adsorbent" chemical reaction reverses and the fluid mixture component reactant is desorbed). A small quantity of purge gas may then be passed over the adsorbent to remove the desorbed component to a collection area. This purge gas stream is now concentrated with the desorbed component. After purging the adsorbent, the original fluid mixture may again be passed over the adsorbent and the cycle repeated.

If the adsorbed (desorbed) component is truly a waste contaminant of the original fluid mixture it can be collected for disposal. But if the component has some value, it can be more easily upgraded or used from this concentrated form than it could in prior processes.

Use of a purge gas is optional since the process is effective in either case. Use without a purge gas is preferred, however, since it generally increases throughput. Without a purge gas, heating causes the desorption and an increase in pressure in the adsorber chamber. This pressure increase causes most of the desorbed component to exit the chamber to be collected. The remaining desorbed component is merely readsorbed when the heating is eliminated and the fluid mixture is again allowed to flow through the adsorber. The readsorption lowers efficiency per cycle but many more cycles can be run without the purge gas since purging requires appropriate valving and time consuming sequenching with the fluid mixture flow. In total, the speed of the regeneration without purging outweighs the slight efficiency advantage enjoyed by purging. Of course, purge gas also dilutes the desorbed component stream.

Separations that are advantageously effected by the method include air separation ($O_2$ production), $CO_2$ and $H_2S$ removal from natural gas, light hydrocarbon separation (replaces distillation), and $SO_2$ or other contaminants from flue gas. Many other separations are possible in practicing the invention.

For purposes of this disclosure the following word meanings will be used. The term microwave frequency radiation is defined as electromagnetic energy in the region of the spectrum having wavelengths of about 1 meter to 1 millimeter and frequencies of about 300 MHz to 300 GHz. However, this energy is conventionally operated in the region of 915, 2450, 5800, or 22,125 MHz in the industrial, scientific and medical (ISM) band as assigned by the Federal Communications Commission. The term radio frequency radiation will mean the same type of energy as microwave but in the lower range of frequencies of about 300 kHz to 300 MHz. The conventional ISM frequencies are 13.56, 27.120, and 40.68 MHz.

Adsorbent shall mean a solid material which has the property of being able to physically or chemically immobilize or adsorb molecules whether or not the adsorbent further enters into a chemical reaction with the adsorbate, as in the "adsorption" of $SO_2$ by ZnO. Molecular sieve as used herein refers to the natural and synthetic crystalline alkali-metal alumino-silicates of the zeolite-type crystalline structure recognized in the art to be adsorbents. The term "noncarbon adsorbent" is intended to include molecular sieves and to exclude adsorbents which consist essentially of carbon, namely activated carbon, charcoal, and the like. For purposes of this disclosure the adsorbents shall have dielectric loss factors not in excess of about 0.1 at operating frequency and be capable of being heated dielectrically. Adsorbents which are selective in any particular separation are well known in the art. For example, see U.S. Pat. No. 4,011,306 which discusses adsorption of oxygen from air with the cobalt chelate, bis (3-fluorosalicylal) ethylenediimine cobalt (II). The present invention is uniquely applicable to noncarbon adsorbents in that adsorbents, which consist essentially of carbon, invariably have been found to be subject to minute electrical spark discharge, i.e. plasma-like electrical sparking, with resultant surface overheating and attrition when subjected to adequate microwave heating for adsorbate removal and adsorbent regeneration.

BEST MODE FOR CARRYING OUT THE INVENTION

The best mode for carrying out the invention is demonstrated by the following examples. However, the benefits to be derived on a commercial scale are much greater since the size of adsorbers is much greater. For example, the laboratory adsorber is 2.5 inches in diameter and 4 inches deep whereas commercial adsorbers can be, for example 3-12 feet in diameter and 3-20 feet deep. Thermal problems and delays with conductive and connective methods of regeneration increase substantially at this scale. Further, the time necessary to heat (and cool) the adsorber is critical to the adsorbent inventory (or the amount of adsorbent needed). Slow heating and cooling necessitates the high capital costs of higher adsorber inventory.

EXAMPLES OF THE PREFERRED EMBODIMENTS

Example 1

To simulate removal of $CO_2$ and $H_2S$ from natural gas, a fluid mixture of $CO_2$ and $H_2S$ in nitrogen was investigated. A source of the fluid mixture analyzing 14.78% $CO_2$ and 6.79% $H_2S$ (balance nitrogen) was connected to the inlet of a 2½ inch (6.35 cm) diameter cylindrical adsorber reactor chamber and a gas flow bellows meter was connected to the outlet thereof. The adsorber was contained within a microwave oven capable of delivering 200-2500 watts of power at 2450 MHz. A nitrogen purge gas source was also connected to the inlet of the adsorber chamber with appropriate valving to admit only one source at a time through the inlet. Thermocouples were removably installed in the adsorber chamber at spaced locations to monitor temperature when microwaves were temporarily turned off.

About 800 grams of molecular sieve 4A was placed in the adsorber column to a depth of about 12 inches (30.5 cm) and the power was turned on to run the column through a heating/cooling cycle to outgas the system. After outgassing the weight of the molecular sieve 4A was determined by difference to be 702 grams.

The adsorbent was then loaded by flowing the gas mixture therethrough for 30 minutes at about 0.5 cubic feet per minute (0.24 l/sec). Total flow through the adsorber was determined from the bellows gas meter to be about 10.5 cubic feet (298 liters). During the loading, samples were taken at elapsed times of 5, 15, 25 and 30 minutes at the outlet of the gas meter for chemical analysis by gas chromatography.

After loading, the gas mixture source was turned off and the adsorber was heated by microwaves at 1000 watts power (150 watts reflected) for 5 minutes. A sample of evolved gases was taken after 3 minutes of heating. The temperature reached 275° C. within the adsorber column. After heating, the pure nitrogen gas source was started at about 0.5 ft³/min (0.24 l/sec) for about 10 minutes to purge the desorbed $CO_2$ and $H_2S$. Samples of this purge gas mixture were also taken for analysis after 0.5 minutes and 10 minutes of purge flow.

Measurements of sample composition indicated that during loading the effluent was substantially pure nitrogen. During heating (desorption), the concentration of $CO_2$ and $H_2S$ in the nitrogen purge gas effluent totaled at least 95%.

Example 2

To quantify results found in Example 1, a second experiment was conducted to measure the degree of concentration which can be achieved in the removal of $CO_2$ and $H_2S$ from a nitrogen carrier gas.

The apparatus was similar to Example 1 using the cylindrical reactor, 1/16 inch pellets of molecular sieve 4A as adsorbent and a source of the fluid mixture analyzing 17.2% $CO_2$ and 5.5% $H_2S$, balance nitrogen.

A quantity of the 4A sieve was placed in the adsorber column and outgassed. The weight thereafter was about 240 grams. The adsorbent was loaded by flowing the fluid mixture therethrough for 27 minutes at 2000 cc/min. Referring to FIG. 1 it can be seen that breakout of $CO_2$ took place after about 5 minutes and breakout of $H_2S$ after about 15 minutes. The bar graph shows the percentage of the components in the effluent stream at various times.

Microwave heating was commenced at t=27 minutes for 8 minutes at 300 watts power. No purge gas was used during this period and for the next 3 minutes thereafter, but it can be seen from the cumulative graph that almost 80% of the adsorbed $CO_2$ and almost 60% of the adsorbed $H_2S$ were desorbed by this time. The $CO_2$ and $H_2S$ during this period made up more than 90% of the effluent gas. The $CO_2$ made up 36-64% of the effluent (versus 17.2% in the original fluid mixture) and $H_2S$ made up 27-56% of the effluent (versus 5.5% in the original fluid mixture). Maximum temperature was about 230° C.

FIG. 1 shows the percentages of the components in the effluent and the cumulative desorption over the period of desorption. Microwave heating was periodically started at 300 watts for 2 minutes at t=45 minutes and 55 minutes and for 2.5 minutes at t=65 minutes. A final heating at 125 watts was initiated at t=76 minutes for 17 minutes. A nitrogen purge of 80 cc/min. was initiated at t=38 minutes to eliminate the remaining desorbed components.

This experiment shows that a substantial amount of the adsorbed component can be removed from the adsorber column without purge gas. Operating commercially, it might be advantageous to begin desorption immediately after break-out (after 5 to 10 minutes in the example), and to end desorption and begin loading again after 80%, for example, of the components have been desorbed.

Example 3

An experiment to separate $CO_2$ and $H_2S$ from methane was conducted using the equipment of Example 1. In the experiment, the 4A molecular sieve was loaded until breakthrough of $H_2S$ occurred as measured by gas chromatographic analysis. After breakthrough, feed gas was interrupted and microwave heating commenced. As the flow of desorbed gases diminished, nitrogen purge gas flow was initiated and followed by intermittent heating cycles to maintain the bed temperature at between about 200° and 260° C. Three load and desorption cycles were run to determine cyclic behavior.

In the first cycle, with a feed gas of 15% $CO_2$, 10% $H_2S$, 0.83% $N_2$, balance $CH_4$, it took 75 minutes at 2000 cc/min to obtain breakthrough of $H_2S$. Flow was stopped and heating at 300 watts was commenced for 8 minutes, followed by a 3 minute pause in heating and another 3 minutes of heating. At this time, a gas analysis showed the composition to be greater than 90% $CO_2$, $H_2S$ and COS. This accounted for almost 100% desorption of $CO_2$ and 30% desorption of the $H_2S$.

On the second load cycle using a methane gas containing 16.2% $CO_2$, 7.2% $H_2S$ and 0.9% $N_2$, it took only 40 minutes to get breakthrough of $H_2S$. Heating at 300 watts for 11 minutes from this point resulted in removal of 68% of the $CO_2$ and 29% of the $H_2S$ from the adsorbent. While heating periodically for a total of 46 minutes during the next 85 minutes at 150 watts to maintain the temperature at about 250° C., a total of 95% of the $CO_2$ and 50% of the $H_2S$ were desorbed.

In the third cycle the feed gas was methane containing 18.5% $CO_2$, 8.6% $H_2S$ and 1.2% $N_2$. Breakthrough of $H_2S$ occurred in 25 minutes and microwave heating thereafter for 11 minutes at 300 watts resulted in 74% desorption of $CO_2$ and 20% desorption of the $H_2S$. Heating for 39 minutes of the next 80 minutes to maintain the temperature resulted in 99% of the $CO_2$ and 36% of the $H_2S$ being removed from the adsorbent.

Example 4

The results of the percentage desorptions in Example 3 were compared with the energy exposure of the adsorbent (the energy exposure being the output power of the microwave generator times the exposure time) to determine the effectiveness of this heating. A comparison experiment was then run with the same loading but with conventional resistance heating to effect the desorption. The energy exposure of the adsorbent during this type of heating was calculated and compared to the percent desorption of $CO_2$, $H_2S$ and $COS$ to determine its effectiveness.

The results showed that the first cycle with microwave heating produced the most effective desorption over the range of 0 to 5000 watt-minutes. The total desorption increased slowly to 25% over 2000 watt-minutes, then accelerated to over 70% within the next 1000 watt-minutes, and finally slowed to a steady desorption rate, reaching almost 100% desorption at 5000 watt-minutes.

The second and third cycles using microwave heating resulted in steady desorption up to 60% desorption after 5000 watt-minutes.

The resistance heating was provided by a 288 watt heat tape and produced desorption which increased steadily to only 20% after 5000 watt-minutes. It might be expected that desorption would begin to increase at a much faster rate if longer times were employed, however, time is a significant factor in throughput and extended times are not desirable on a commercial scale.

Further, the temperature of the adsorbent near the wall was much hotter during the resistance heating, raising the problem of damage to the adsorbent if excessive power is employed in resistance heating. Moreover, the hotter the adsorber, the longer the cooling time which would be necessary to begin another cycle, again adversely affecting throughput.

Example 5

An experiment was conducted to show the ability to recover $SO_2$ sorbate from a sorbent.

An effective $SO_2$ sorbent was prepared by reacting $ZnO$ with $SO_2$ and $H_2O$ to form $ZnSO_3.2\frac{1}{2} H_2O$ and then driving off the $SO_2$ and $H_2O$ by heating. The $ZnO$ is an effective sorbent for $SO_2$ when $H_2O$ is present, and after the above pretreatment, is much more effective in sorbing $SO_2$ than is $ZnO$ without the treatment. The increase in efficiency is probably due to a surface area increase.

82 grams of the pretreated zinc oxide was slurried with 360 ml of water and placed in an adsorber chamber such as in Example 1. Pure $SO_2$ gas was then bubbled through the slurry for about 30 minutes at about 2 grams/minute. The adsorbent was then dried overnight at about 90°-98° C. and weighed 138.8 grams for a weight gain of 56.8 grams $SO_2$.

This saturated sorbent was then heated dielectrically as in Example 1 for $4\frac{1}{2}$ minutes at 1000 watts power (350 reducing to 100 watts reflected). The offgas was analyzed and found to be essentially pure $SO_2$. This shows that a sorbent can be rapidly regenerated and the offgas stream can be highly concentrated in the desorbed gas.

Example 6

The apparatus of Example 1 was modified by placing the bellows meter before the adsorption column and a wet test meter at the output side of the column. This provided more accurate loading and desorption flows from the separation of this example. A 13X molecular sieve was employed in the column to adsorb $C_2$, $C_3$ and $C_4$ hydrocarbons from the impure methane feed. The feed gas analyzed 81.6% $CH_4$, 10.5% $C_2H_6$, 5.3% $C_3H_8$ and 2.6% $C_4H_{10}$.

The feed gas was started at $t=0$ and continued at 2450 cc/min. until $t=86$ minutes when about 5% propane breakthrough occurred. During the loading, ethane was not totally adsorbed. It made up about 15% of the output with the balance being methane. Selection of a better adsorbent or a second adsorption would separate the ethane and leave essentially pure methane.

At $t=86$ minutes, microwave heating was commenced at 300 watts for 7.5 minutes, followed by a 1 minute pause, 2 minutes of heating, a 2 minute pause and 2 more minutes of heating. During this time 5075 cc of the adsorbed ethane and propane gases were desorbed. The composition of the offgas was between 85 and 97% ethane plus propane with the balance methane. Continued periodic heating with microwaves using a nitrogen purge produced an offgas mixture comprising 30-40% propane and butane with the balance nitrogen.

A second loading at 2450 cc/min. of the adsorbent resulted in a 5% propane breakthrough after 63 minutes. Eleven minutes of microwave heating at 300 watts followed by a 1 minute pause and 3 minutes additional heating desorbed 5800 cc of the $C_2-C_4$ gases and resulted in a gas which was 95% $C_2-C_4$. Intermittent heating over an additional 90 minutes removed a cumulative total of about 11,400 cc of the adsorbed gases.

Example 7

The experiment of Example 6 was continued with a third loading/desorption cycle but for comparison using resistance heating in place of dielectric heating to desorb the adsorbed gases. A 288 watt resistance heating tape was wrapped around the adsorber column and heating equivalent to the microwave energy input to the adsorber was used.

A feed gas similar to the gas of Example 6 but analyzing 80.5% $CH_4$, 10.1% $C_2H_6$, 3.0% $C_3H_8$, 3.8% $C_4H_{10}$ and 0.6% $N_2$ was used. A loading rate of 2450 cc/min. was used for 71 minutes. Resistance heating was initiated for 38 minutes during which the gas composition approached 95% $C_2C_4$. However, during the first 12 minutes, only about 3300 cc of gases were desorbed. This is due at least in part to the poor thermal transport and conductivity inherent in this type of heating.

Example 8

Apparatus as used in Example 6 was used to separate $O_2$ and $N_2$ from air. A 5A molecular sieve was used to adsorb the nitrogen.

The adsorbent column was first saturated with 98% $O_2$ and then air was passed therethrough and the oxygen rich offgas collected until the exit stream contained only 30% $O_2$ (70% nitrogen). At this time the adsorbent was heated with microwaves at 500 watts power. During the first 2.5 minutes of heating a large percentage of the nitrogen was desorbed and the offgas increased from 70% N$_2$ to about 82% N$_2$. Thereafter, less gas was desorbed but the nitrogen content increased to 94% after 10 minutes of heating. The final temperature of the column was about 125° C.

The data show that nitrogen and oxygen can be separated using the invention. The results are believed to be conservative in that a lag in measuring the composition of the offgas may be present because of the physical separation of the flow meter and the downstream gas chromatograph. Therefore the large volume of gas desorbed in the first 2.5 minutes may in fact be much higher in nitrogen than recorded.

Example 9

For comparison purposes an experiment was made to use microwave heating to desorb a mixture of organic liquid solvents which had been adsorbed by a sorbent of activated carbon granules.

About 150 g. of activated carbon granules, after outgassing and driving of water therefrom by microwave heating, were used. Nitrogen gas at a rate of about 1500 cm$^3$/min. was bubbled through a container, which was filled with glass beads and the organic liquid solvent mixture, and then through the activated carbon granules until gas chromatographic sampling showed a breakthrough of organic solvent in the gas exiting from the granules and with apparently no significant additional solvent mixture being absorbed by the carbon granules sorbent. At this time the carbon sorbent loading was estimated to be about 16 percent by weight of absorbed organic liquid solvents mixture. The organic liquid solvent mixture used consisted, in parts by weight, essentially of about: 27.6 xylene; 2 butanol; 9.2 diacetone alcohol; 26.5 mineral spirits; 7.1 methyl isobutyl ketone; 3.1 methyl ethyl ketone; 2 cellosolve acetate; 2 butyl cellosolve; 17.4 toluene; 2 isopropanol; and 1 propylene oxide.

Carbon regeneration and desorption of the absorbed organic liquid solvent mixture was attempted by microwave heating twice using 300 watts first for 14 minutes and then for 12 minutes, respectively. The center of the mass of granules reached about 250° C. for each heating. During the microwave heatings there were observed minute electrical spark discharges occurring between granules and also some incandescence or glowing appearance of the granules' surfaces. Nitrogen gas at about 100 cm$^3$/min. was passed through the microwave-heated carbon granular absorbent and then into an about $-78°$ C. cold trap. Analysis of the gas exiting from the cold trap showed a significant amount of hydrogen in the exiting nitrogen to indicate significant cracking of the desorbed solvents. The total material collected in the cold trap amounted to only about 20 percent by weight of the weight of the organic liquid solvents mixing absorbed by the activated carbon granules. Additionally the cold trap collected material had an odor unlike that of the starting mixture of organic liquid solvents. An examination of the activated carbon granules after this experiment revealed attrition and some pitting of surfaces of granules.

From the foregoing examples, it is apparent that the invention provides a process for the rapid, efficient regeneration of a saturated solid noncarbon adsorbent without thermal or mechanical degradation of the adsorbent through heating the adsorbent internally and in the absence of spark discharges with microwaves in the adsorber reactor chamber and in the absence of added activating or regenerating gas to a temperature sufficient to desorb the adsorbate. Preferably the adsorbent is a molecular sieve 4A, 5A, or 13X or zinc oxide with the desorbed absorbate comprising hydrogen sulfide and carbon dioxide when the adsorbent be molecular sieve 4A, ethane and propane when the adsorbent be molecular sieve 13X, oxygen and nitrogen when the adsorbent be molecular sieve 5A, and sulfur dioxide when the adsorbent be zinc oxide.

We claim:

1. A process for the rapid, efficient regeneration of a saturated solid noncarbon adsorbent without thermal or mechanical degradation of the adsorbent which comprises heating the adsorbent internally and in the absence of spark discharges with microwaves between 300 MHz and 300 GHz frequency in the adsorber reactor chamber and in the absence of added activating gas to a temperature sufficient to desorb the adsorbate.

2. The process of claim 1 wherein the adsorption includes a chemical reaction of the adsorbate with the adsorbent which comprises heating the adsorbent to a temperature sufficient to drive the chemical reaction in reverse and desorb the adsorbate.

3. The process of claim 1 wherein a concentrated stream of the desorbed adsorbate is recovered which comprises, after heating the adsorbent, passing a volume of purge gas sufficient to carry away the desorbed absorbate across the adsorbent and collecting the effluent purge gas and desorbed adsorbate.

4. The process of claim 1 wherein the adsorbent is a molecular sieve.

5. The process of claim 1 wherein the adsorbent comprises zinc oxide and the adsorbate comprises sulfur dioxide.

6. The process of claim 1 wherein the adsorbent comprises molecular sieve 4A and the adsorbate comprises hydrogen sulfide and carbon dioxide.

7. A process for rapidly separating a fluid mixture into two concentrated streams by an adsorption-regeneration process which comprises:

(a) passing said fluid mixture in contact with a solid noncarbon adsorbent in an adsorber reactor chamber to preferentially adsorb at least one chemical component of said mixture;

(b) collecting a concentrated first fluid stream which remains from said fluid mixture after absorption of said chemical component by said absorbent;

(c) temporarily halting the flow of said fluid mixture passing in contact with said adsorbent;

(d) heating said absorbent internally and in the absence of spark discharges and in the absence of added activating gas in the adsorber reactor chamber with microwaves between 300 MHz and 300 GHz frequency to a temperature at which said adsorbed chemical component is desorbed from said adsorbent material, and (e) collecting a concentrated second fluid stream comprising said desorbed chemical component.

8. The process of claim 7 wherein the adsorption includes a chemical reaction of the adsorbate with the adsorbent which comprises heating said absorbent to a temperature sufficient to drive said adsorption reaction in reverse and desorb said adsorbate.

9. The process of claim 7 wherein said desorbed chemical component is purged from said adsorbent after desorption which comprises passing a quantity of purge gas across said adsorbent sufficient to remove said desorbed chemical component from contact with said adsorbent, and collecting said concentrated second fluid stream comprising said desorbed chemical component and said purge gas.

10. The process of claim 7 wherein, said fluid mixture comprises methane and said chemical component comprises carbon dioxide and hydrogen sulfide and is purged from said adsorbent, which is molecular sieve 4A, and after desorption which comprises passing a quantity of purge gas across said adsorbent sufficient to remove said desorbed chemical component from contact with said adsorbent, and collecting said concentrated second fluid stream comprising said desorbed chemical component and said purge gas.

* * * * *